(12) United States Patent
Horras et al.

(10) Patent No.: US 11,207,009 B2
(45) Date of Patent: Dec. 28, 2021

(54) INTERMITTENT MEASURING OF THE PARTIAL PRESSURE OF AN ANALYTE IN THE SKIN TISSUE

(71) Applicant: RADIOMETER BASEL AG, Basel (CH)

(72) Inventors: Mathieu Horras, Basel (CH); Franz Von Wirth, Basel (CH)

(73) Assignee: RADIOMETER BASEL AG, Basel (CH)

( * ) Notice: Subject to any disclaimer, the term of this patent is extended or adjusted under 35 U.S.C. 154(b) by 686 days.

(21) Appl. No.: 15/326,072

(22) PCT Filed: Jul. 13, 2015

(86) PCT No.: PCT/EP2015/065959
§ 371 (c)(1),
(2) Date: Jan. 13, 2017

(87) PCT Pub. No.: WO2016/008840
PCT Pub. Date: Jan. 21, 2016

(65) Prior Publication Data
US 2017/0196489 A1  Jul. 13, 2017

(30) Foreign Application Priority Data
Jul. 15, 2014  (DK) .............................. PA2014/00383

(51) Int. Cl.
*A61B 5/1491* (2006.01)
*A61B 5/145* (2006.01)
(Continued)

(52) U.S. Cl.
CPC .......... *A61B 5/1491* (2013.01); *A61B 5/1477* (2013.01); *A61B 5/14542* (2013.01); *A61B 90/03* (2016.02); *A61B 5/6813* (2013.01)

(58) Field of Classification Search
None
See application file for complete search history.

(56) References Cited

U.S. PATENT DOCUMENTS 4,230,122 A   10/1980  Lübbers et al.
4,252,123 A *  2/1981  Kimmich ........... A61B 5/14542
                                                204/403.06
(Continued)

FOREIGN PATENT DOCUMENTS

CN   102843967 A   12/2012
CN   106659397 A    5/2017
(Continued)

OTHER PUBLICATIONS

English language abstract for EP 0 314 027, May 3, 1989.
(Continued)

*Primary Examiner* — Matthew Kremer
(74) *Attorney, Agent, or Firm* — Finnegan, Henderson, Farabow, Garrett & Dunner, LLP

(57) ABSTRACT

It is commonly known within the art of cutaneous/transcutaneous blood gas monitoring to warm up the skin of the patient to allow carbon dioxide and oxygen to diffuse easily through the skin. This is especially the case for transcutaneous partial pressure monitoring of oxygen. Heating the skin to 43° C. to 45° C. over several hours or days may cause damage to the skin. In order to avoid or minimize the risk of these damage, it is proposed to monitor the blood gases at a lower temperature with a cutaneous sensor, and intermittently warm up the skin to a temperature of 42° C. or more for a short duration to monitor the transcutaneous partial pressure of oxygen, before lowering the temperature to the lower set point.

8 Claims, 3 Drawing Sheets

(51) Int. Cl.
*A61B 5/1477* (2006.01)
*A61B 90/00* (2016.01)
*A61B 5/00* (2006.01)

(56) References Cited

U.S. PATENT DOCUMENTS

| | | | |
|---|---|---|---|
| 4,265,250 A | | 5/1981 | Parker |
| 4,539,994 A | * | 9/1985 | Baumbach .......... A61B 5/14542 |
| | | | 204/403.06 |
| 4,586,149 A | * | 4/1986 | Stillman .............. A61B 5/1491 |
| | | | 374/163 |
| 2002/0062070 A1 | * | 5/2002 | Tschupp ............... A61B 5/0002 |
| | | | 600/322 |
| 2008/0064942 A1 | * | 3/2008 | Gisiger .............. A61B 5/14539 |
| | | | 600/354 |

FOREIGN PATENT DOCUMENTS

| | | |
|---|---|---|
| DE | 2 305 049 | 8/1974 |
| EP | 0336201 A | 3/1989 |
| EP | 0 314 027 | 5/1989 |
| JP | 56-8040 | 1/1981 |
| JP | 57-196965 | 12/1982 |
| WO | WO 92/12670 | 8/1992 |

OTHER PUBLICATIONS

International Search Report of International Application No. PCT/EP2015/065959, dated Sep. 14, 2015.
Written Opinion of the International Searching Authority for International Application No. PCT/EP2015/065959.

* cited by examiner

INTERMITTENT MEASURING OF THE PARTIAL PRESSURE OF AN ANALYTE IN THE SKIN TISSUE

This application is a national stage filing under 35 U.S.C. § 371 of International Application No. PCT/EP2015/065959, filed on Jul. 13, 2015, which claims priority of Danish Patent Application No. PA2014/00383, filed Jul. 15, 2014. The contents of these applications are each incorporated herein by reference.

The present invention relates to a system and method for non-invasive, in-vivo determination of the partial pressure of an analyte in the blood, and tissue, in particular the transcutaneous partial pressure of oxygen ($O_2$). The system comprises a sensor for measuring carbon dioxide ($CO_2$) and/or oxygen ($O_2$), a monitor showing the readout of the measured analyte, and suitable connectivity between the sensor and the monitor, e.g. wired or wireless.

It is well known to continuously measure blood gases using electrochemical sensors that heat the skin to get a transcutaneous measurement of the blood gases. By heating the sensor, the skin of the patient is also heated, whereby the skin is arterialized. The skin is heated to increase the cutaneous blood flow, and hence the transcutaneous partial pressure of oxygen increases and the carbon dioxide partial pressure decreases, whereby the measurements of blood gas partial pressure reflects and correlates better with the arterial partial pressure of blood gases. However since patients are usually monitored over longer periods of time, increasing the temperature may easily lead to burn marks on the skin of the patient, also known as erythema. This is especially a problem for preterm neonates, whose skin is very thin and very fragile, and hence sensitive to heating.

The problem of skin erythema when measuring blood gas levels is due to two factors. One is the actual temperature of the sensor, for arterializing the capillary bed in the skin tissue beneath the sensor. The sensor temperature sufficient for arterializing the capillary bed depends to a large degree on the tissue. The second factor that may contribute to erythema is the measuring time. Often blood gas monitors are used for critically ill patients or neonates at Neonates Intensive Care Units (NICU), where the patient is monitored for several days or even weeks. When heating the skin for this long time, heating the sensor to temperatures only a few degrees above the skin temperature may cause a fragile skin to be burned.

To avoid skin erythema, one solution has been for the care takers to move the sensors around to different locations on the body. A typical measuring time at the same place is two-to-four hours with a sensor temperature in the range of 42° C.-44° C. Replacing the sensors every two-to-four hours is cumbersome and time consuming for the caretakers, and may also decrease the reliability of the measurements. Furthermore applying fixation rings for fixing the sensors to the skin increases the risk of injuring the patient when the fixation rings finally has to be removed again. Even Further in the effort to eliminate the risk of skin burns by moving around the sensors, the care takers may choose locations on the body, which are less suitable for the purpose, i.e. locations where the skin is thicker and less permeable to blood gases, which then increases the risk of getting unreliable measurements. Furthermore, especially for neonates, suitable sites for placing a sensor is limited due to limited area of skin with a large enough flat surfaces, where the sensor can be positioned. Also areas with underlying weak bones, that may easily be broken, applying the fixation ring, or the sensor, are to be avoided.

U.S. Pat. No. 4,252,423 disclose a transcutaneous electrochemical sensor for determining the oxygen transcutaneous partial pressure in blood. The sensor has at least three measuring cells of the Clark type comprising periodically actuated heating elements, the heating elements being actuated at a phase difference, such that always at least one cell provides a reliable measuring value. Such a device has the drawback that it becomes large and cumbersome, because it includes three measuring cells which makes it useless for measuring at the earlobe, which is a preferred measuring site, and even more useless for the use on neonates. Further, to provide a reliable reading at least two heating elements are overlapping in time, thus supplying twice the amount of power to the tissue covered by the two adjacent heating elements.

U.S. Pat. No. 4,230,122 disclose a system for determining the perfusion efficiency in tissue through which blood is being perfused. To do this it is relevant to determine how well the skin breaths and how large the contribution from the surroundings is. To determine this, the sensor is kept at a low temperature corresponding to the body temperature, where it is known that there is no perfusion through the tissue of oxygen. The measured oxygen concentration at this temperature is used as a reference value, as the oxygen in the capillaries does not influence the measured value at body temperature. Hence the determined value shows the outer most lay of the skin ability to breath, i.e. to take up oxygen from the surroundings.

The risk of skin erythema is generally more problematic when measuring the transcutaneous partial pressure of oxygen since oxygen does not diffuse easily through the skin. The stratum corneum, which is the outermost layer of the epidermis, consisting of dead skin cells, acts as a membrane keeping the oxygen inside the body, where it is needed for the organisms to work. The stratum corneum further protects the underlying tissue from infection, dehydration, chemicals and mechanical stress, but allows the carbon dioxide to diffuse through the skin. By heating the stratum corneum to a temperature above the skin temperature, and more specifically to at least 42° C., the stratum corneum is made more permeable to oxygen. In more medical terms this is known as dissolving the lipid structure of the dead, keratinized cells in the epidermal layer. For current sensors for measuring transcutaneous partial pressure of oxygen, the sensor should remain on site for approximately 10 to 15 minutes at least at 43° C., before the measurements are considered accurate.

In an aspect of the invention, a system for monitoring the transcutaneously measured partial pressure of oxygen at a measuring site of a patient is provided. The system comprises a monitor for displaying the measured partial pressure of oxygen, a sensor for measuring the transcutaneous partial pressure of oxygen comprising a heating element for heating the skin at the measuring site, communication means for communicating between the sensor and the monitor, control means for controlling the temperature of the heating element, the control means is further adapted for cycling the temperature between two different temperatures; a first time interval at which the measuring site has a close to body core temperature, and a second time interval, at which the measuring site has a temperature where the skin is permeable to oxygen in an outward direction from the tissue or blood to the surroundings, the transcutaneous partial pressure of oxygen is measured at the second time interval, and the first time interval is longer than the second time interval.

By cycling the temperature, the total time the skin is exposed to high temperatures is lowered. Hereby the risk of erythema is reduced or alternatively it is possible to increase the temperature without increasing the risk of erythema. Compared with moving sensors around to different measurement sites, the advantage with the proposed solution is that it is more efficient for the hospital staff and sensors may be kept on the preferred measurement sites throughout the entire measurement. Furthermore, moving the sensors around may require recalibration of the sensor and waste of electrolyte solution and contact gel, since keeping the sensor at one site in a closed measurement volume would no waste as much electrolyte and contact gel. In an embodiment of the first mentioned aspect, the first temperature is in the range 35° C. to 42° C., and the second temperature is at least 41° C.

At temperatures of 35° C. to 42° C. the risk of erythema is low.

In an embodiment of the first mentioned aspect, the measured partial pressure of oxygen is shown at the monitor at all times, and during the first time interval the shown value is the last partial pressure of oxygen measured at the previous second time interval.

The nurse or other care taker at the hospital may come by the patient at frequent intervals. However not necessarily during the time of the cycle where the partial pressure of oxygen is measured. By displaying the last measured partial pressure, measured during the first time interval with a temperature sufficient to make the skin permeable to skin, the nurse is able to see the partial pressure of oxygen without having to wait by the patient for the next time interval. Furthermore these measurements rarely change abruptly unless there is another problem, monitored in other ways.

In and embodiment of the first mentioned aspect, the system is further continuously monitoring the partial pressure of carbon dioxide (CO2).

This provides a real time picture of the partial pressure of carbon dioxide. Partial pressure of carbon dioxide and oxygen are often interdependent. Hence a change in the partial pressure of carbon dioxide may be an indication that the partial pressure of oxygen should be covered more closely.

In an embodiment of the first mentioned aspect, the system for monitoring the transcutaneously measured partial pressure of oxygen is further adapted for allowing the operator to adjust the time of the first and the second time interval.

Depending on the criticality, the stability and the history of the patient the medical staff would like to get the oxygen partial pressure at different intervals, such that the risk of erythema is balanced against the urgency of frequent measurements of the oxygen partial pressure.

In another aspect of the invention a sensor for transcutaneously measuring the partial pressure of oxygen at a measuring site of a patient is provided. The sensor comprises a heating element, for heating the measuring site, a control unit for controlling the temperature of the measuring site, processing of the sensor signals, and controlling communication between the sensor and a monitor. The control unit comprising an analogue to digital converter, and further being adapted to control the heating element to cycle the temperature at a measuring site of a patient between two different temperatures by; adjust and maintain the measuring site at a temperature close to body core temperature in a first time interval, and increase and maintain the measuring site at a temperature wherein the skin is permeable to oxygen in an outward direction from the tissue or blood to the surroundings in a second time interval. The first time interval is longer than the second time interval, and the sequence of first and second time intervals is repeated.

Depending on the type of sensor used for the measurement, the controlling elements may be placed either in the monitor or in the sensor. Traditionally the controlling elements have been placed in the monitor but with miniaturization falling prices of electronics it has become more attractive to place more electronic and signal processing in the sensor. Among other things this allows the communication between the sensor and the monitor to be digital communication, wired or wireless.

In an embodiment of the second mentioned aspect, the temperature at the measuring site in the first time interval in maintained at 35-42° C., and in the second time interval is maintained at, at least 41° C.

In yet another aspect of the invention a computer program product for controlling an oxygen sensor for measuring a transcutaneous partial pressure of oxygen is provided. The computer program product is adapted to control a heating element of the oxygen sensor to; cycle the temperature at a measuring site of a patient between two different temperatures. Adjust and maintain the measuring site at a temperature close to body core temperature in a first time interval, and increase and maintain the measuring site to a temperature wherein the skin is permeable to oxygen in an outward direction from the tissue or blood to the surroundings in a second time interval. The first time interval is longer than the second time interval, and the sequence of first and second time intervals is repeated.

Providing the invention as a computer program allows that existing sensors and monitors be fitted with this feature.

In an embodiment of the computer program product, the second time interval comprises at least 10 minutes of heating up the skin for dissolving the lipid structure, followed by 5 minutes of measuring the oxygen partial pressure.

10 minutes for heating up the skin has been found to be an acceptable time to dissolve the lipid structure of the skin the limit amount of power available in a transcutaneous sensor and without overheating by further increasing the temperature, which would again increase the risk of erythema. When the lipid structure of the skin has been dissolved the system comprising sensor and skin needs a little time to stabilize before stable measurements can be performed. 5 minutes has been found to be sufficient for stabilization and conducting a number of measurements also showing the measurement of the partial pressure of oxygen shows consistent measurements.

In an embodiment of the computer program product the first time interval is at least 20 minutes.

To effectively reduce the power subjected to the skin, the first time interval, where the temperature is close to body core temperature should preferably be longer than the time where the skin is heated to become permeable to oxygen.

In an embodiment of the computer program product the computer program product evaluates whether the measured partial pressure of oxygen is stable before communicating the measured partial pressure is being communicated to the operator.

Once the measurement site is heated the sensor is able to conduct several measurements within a short time frame, but since the first measurements may fluctuate since the system has not stabilized yet, these are evaluated as to whether they show consistent values, before they are communicated to the operator. Furthermore, the partial pressure of oxygen may be measured at temperatures where the reliability of the measure values is small. In such cases the monitor may communicate to the hospital staff what the measured value is, but at the same time indicate that this value is not measure under stable conditions to make the staff aware of the reliability of the measurement. Further this may be used for providing the staff with a reliability index of the measured value, where the reliability is calculated based on the history of measurements e.g. time and number of measurements compared to the consistency of the measured values.

In a further embodiment, the computer program product communicates the measured partial pressure of oxygen to the monitor as speech and/or text.

In yet another aspect of the invention, a method for monitoring the transcutaneous partial pressure of oxygen (tcpO2) at a measuring site of a patient is provided. The method comprising the steps of; cycling the temperature at the measuring site between two different temperatures adjust and maintain the measuring site at a temperature close to body core temperature in a first time interval, and increase and maintain the measuring site to a temperature wherein the skin is permeable to oxygen in an outward direction from the tissue or blood to the surroundings in a second time interval, and measuring the partial pressure of oxygen in the second time interval. The first time interval is longer than the second time interval.

The risk of erythema is reduced or alternatively it is possible to increase the temperature without increasing the risk of erythema. Compared with moving sensors around to different measurement sites, the advantage with the proposed solution is that it is more efficient for the hospital staff and sensors may be kept on the preferred measurement sites throughout the entire measurement. Furthermore, moving the sensors around may require recalibration of the sensor and waste of electrolyte solution and contact gel, since keeping the sensor at one site in a closed measurement volume would no waste as much electrolyte and contact gel.

In an embodiment of the method, the partial pressure of $CO_2$ is measured continuously.

Since the diffusion of $CO_2$ through the skin is less affected by the temperature of the skin at the measuring site, the transcutaneous partial pressure of $CO_2$ may be calculated from the sensor signal irrespective of the temperature of the skin at the measuring site.

In an embodiment of the method, the measuring of the partial pressure of $CO_2$ takes the cycling temperature into account when calculating the partial pressure of $CO_2$. The diffusion varies with the temperature of the skin, but this may be taken into account when calculating the partial pressure of $CO_2$.

In an embodiment of the method the partial pressure of oxygen measured during the previous second time interval, is shown at the monitor during the following first time interval.

Although a value of the partial pressure of oxygen may be measured with the sensor during the first time interval, the measured partial pressure will not reflect the arterial partial pressure, since the skin is partly or fully blocking the diffusion of oxygen. It is thus more relevant for the hospital staff to be able to see the partial pressure of oxygen measured when the skin was last permeable to oxygen.

In an embodiment of the method the temperature at the measuring site in the first time interval is 35-42° C., and the temperature at the measuring site during the second time interval is at least 41° C.

The risk of erythema is low at temperatures close to body core temperature.

The sensor may continuously measure the carbon dioxide partial pressure, or other blood gases at a temperature close to the body or skin temperature. At discrete time intervals, the sensor heats up the skin to arterialize the capillary bed, whereby oxygen starts to diffuse more easily through the skin. At least one measurement of the transcutaneous partial pressure of oxygen is made, while the skin is heated, before the control circuit again regulates the temperature of the heating element to the low set temperature, allowing the skin to cool down to a temperature primarily controlled by the blood flow in the skin. In this way, the sensor continuously measures the carbon dioxide level, which is also continuously shown at the monitor, corrected for the applied temperature. The partial pressure of oxygen may also be measured continuously, but the monitor shows the last valid measurement, i.e. a valid measurement done at the high temperature.

The function of intermittent heating may be a fixed preprogrammed function where the sensor is heated for e.g. 10 minutes, to allow the tissue beneath the sensor to fully warm up, followed by e.g. 5 minutes of measuring the oxygen level followed by e.g. 30 minutes at the low temperature, where the oxygen level measured is known to be less reliable. It may be optional to actually show the measured partial pressure of oxygen during the period of low temperature.

In an alternative embodiment the user may to some degree define the timing as long as minimum time for, heating up the skin, measuring the oxygen transcutaneous partial pressure, and low temperature measurements are above the minimum time settings e.g. 10 minutes for warming up the skin to dissolve the lipid structure, 5 minutes for measuring the oxygen partial pressure at stable conditions, and 20 minutes where the temperature is regulated to the low set point.

In an embodiment, the oxygen partial pressure is measured constantly, even when the temperature is too low. The control system, whether located in the sensor or in the monitor, determines when the transcutaneous partial pressure of oxygen is stable, where after the level is shown on the monitor. Alternatively, the level measured is always shown, followed by an indicator of whether a stable level has been reached.

The transcutaneous partial pressure of carbon dioxide ($CO_2$) may be measured and displayed at the monitor continuously and simultaneously with the transcutaneous partial pressure of oxygen. The readout on the monitor is then dynamically adjusted according to the present temperature, as is known in the art.

The lungs of the fetus are not used for ventilating the blood. The blood is ventilated in the lungs of the mother, the blood circulation in the fetus is by-passing the lungs via a cardiac shunt that is closed during birth. To detect whether these shunts are closed (Coarctation of the aorta), sensors are often placed at the right arm and left foot.

Figure 1:
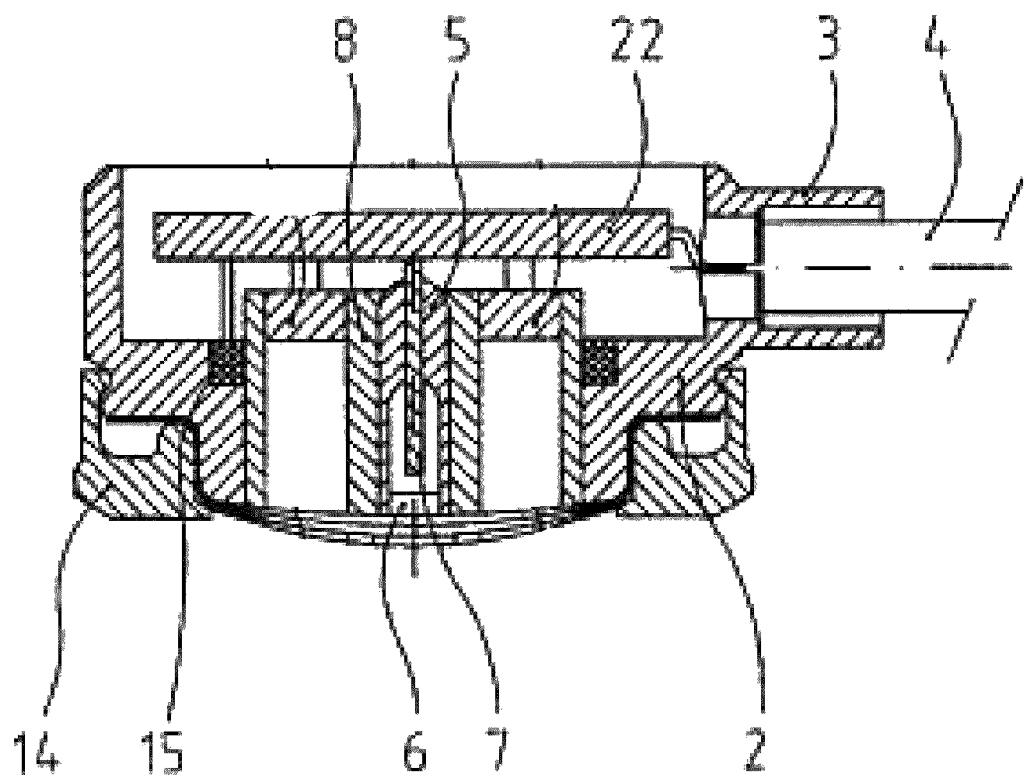
FIG. 1 shows a sensor according to the invention

FIG. 1 shows a blood gas sensor for transcutaneous or cutaneous measurements of blood gases. The sensor head consist of a circular plastics housing 2 with a neck like attachment 3 through which the connecting cables 4, for transferring analogue or digital signals to the monitor, are led. A glass pH electrode 5 is located in the central axis of the sensor. It comprises a glass stem onto whose front end a pH-sensitive glass layer 6 is fused. An internal reference electrode with a platinum lead wire 7 fused into the glass is located inside the glass cylinder. The pH electrode 5 is embedded in a silver block 8 whose surface is covered with a chloride layer. The surface of the silver block thus forms an Ag/AgCl electrode which acts as reference electrode for the pH measurement. An electrolyte solution whose pH will be measured is located on a porous hydrophilic spacer, covered with a gas permeable hydrophobic membrane. To protect the membrane from mechanical damage, it is covered with a metal diaphragm. This diaphragm has in the center an aperture through which the carbon dioxide gas to be measured is able to diffuse into the electrolyte solution at the site of the pH-sensitive glass layer. The spacer, the membrane, and the metal diaphragm are attached to the sensor housing 2 by means of a clamping ring 14. The silver block 8 additionally has the function of a heating element. A heating wire 15 is coiled around it and heats it to the temperature of up to 45° C.

The sensor may further include a control block, which is not shown in the drawing, for control and processing of the signals measured by the sensor, and distribute signals to or from the monitor.

Figure 2:
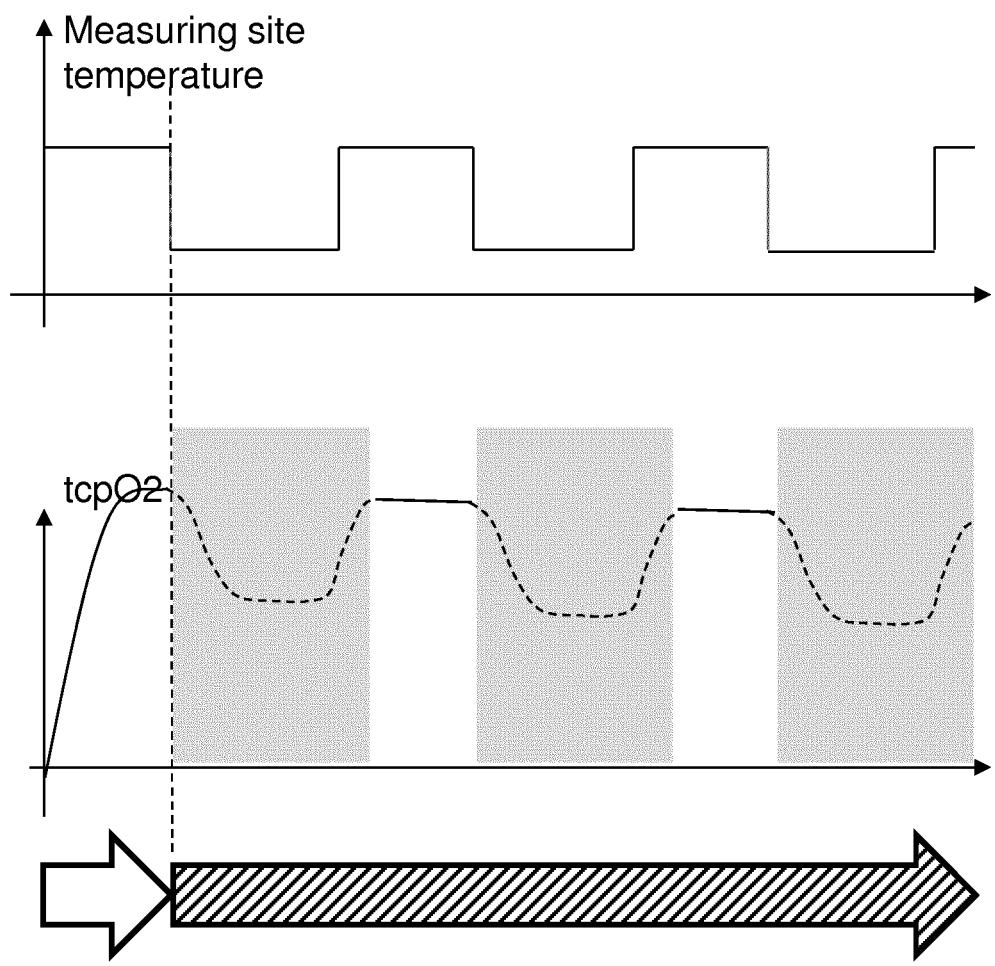
FIG. 2 shows two graphs of the $O_2$ measurement, and the heating interval respectively.

FIG. 2 shows two graphs. One indicating the sensor temperature as a function of time and below a diagram of the oxygen level measured over time. The first period of time indicated by the vertical dashed line and also by the non-scattered arrow below the diagrams represent the warm-up phase, where it is usually not advisable to measure, since the measurements may not be reliable. After the initial warm-up phase, the sensor heating element regulates the temperature with predetermined intervals, whereby the sensor temperature and hence the skin temperature fluctuates. When the temperature is low, the oxygen levels measured are less reliable, than when the temperature is high. Thus the transcutaneous partial pressure of oxygen is measured at the time, when the temperature of the skin is sufficient to ensure a reliable measurement. The curved line shows the transcutaneous partial pressure of oxygen over time. The line is solid when the temperature is sufficient for reliable measures and dotted, when the temperature is such that the measures cannot be relied upon directly. Under normal circumstances, the skin will be subjected to the higher temperature for at least 10 minutes, to warm up the capillary bed sufficiently, where after the oxygen tension may be measured for e.g. 5 minutes. The heating element is now turned off, allowing the temperature to drop back to the lower temperature, where it is kept for e.g. 30 minutes before warming up again to get a new set of oxygen partial pressure measurements at the higher temperature, starting a new cycle.

Figure 3:
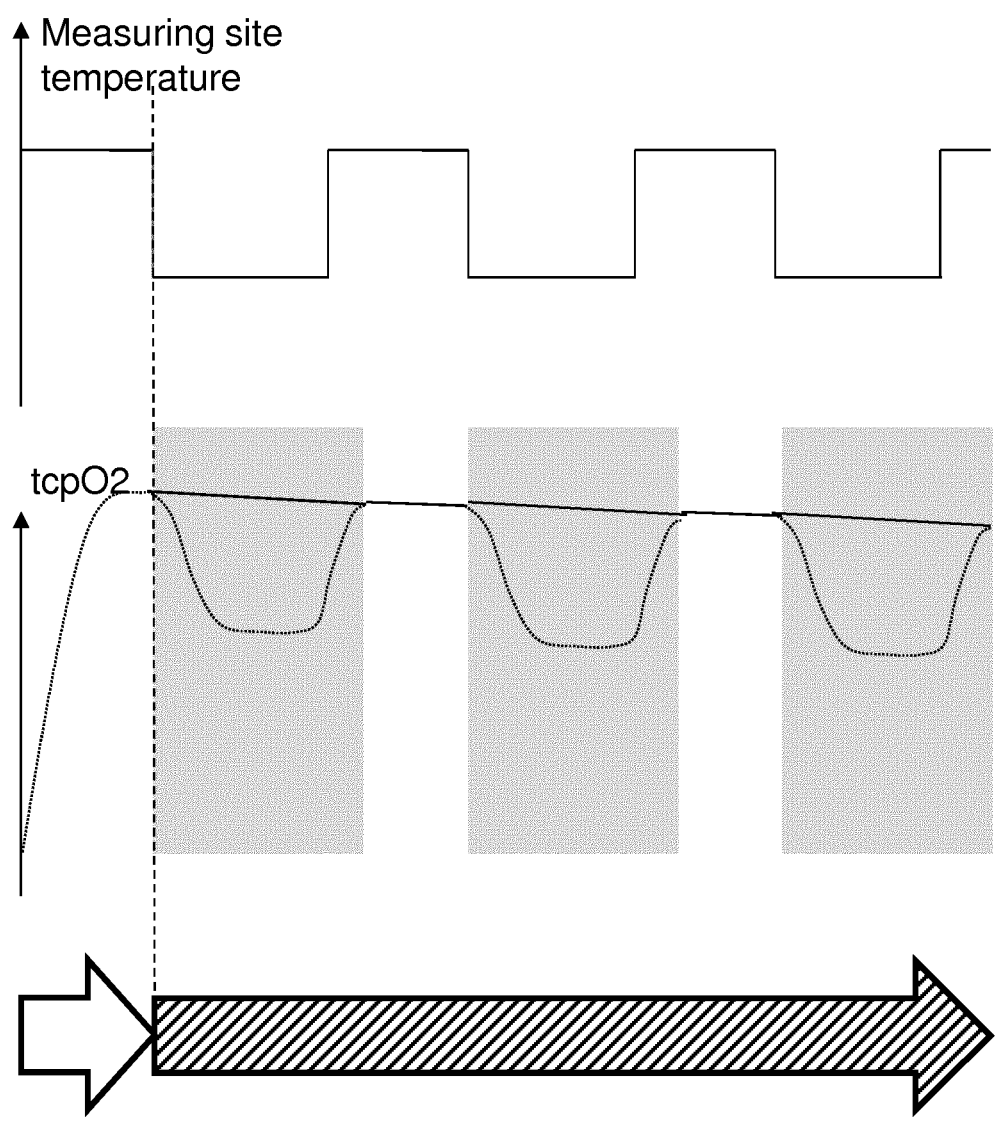
FIG. 3 shows two graphs of the transcutaneous partial oxygen pressure measured.

FIG. 3 shows another embodiment, where the transcutaneous partial pressure of oxygen is still shown at the instances with a low skin temperature. The level shown is in this case extrapolated from the previous one or more levels measured. The dashed line is the actual oxygen level measured and the solid line is a combination of the levels measured, when the temperature is sufficient, and the extrapolated level in between. The care taker is hereby made aware, that the shown level is not the actual current oxygen transcutaneous partial pressure, but a value extracted from the previously measured levels.

To further explain the invention, an example of the use of the proposed method, system and device will be given in the following. A premature infant is intubated and mechanically ventilated at a neonate intensive-care unit (NICU). To monitor the neonate's respiratory function, the NICU nurse applies a blood gas monitor to the neonate. The monitor includes sensors for measuring the transcutaneous partial pressure of oxygen and carbon dioxide. The sensor is mounted in a fixation ring, fixing the sensor to the skin with a contact gel between the skin and the sensor interface to create a closed measuring chamber between the skin and the sensor. Wires transfer data between the sensor and the monitor. The NICU nurse would like to receive information about both oxygen and carbon dioxide transcutaneous partial pressure. To minimize the risk of injury, the nurse chooses the default program for monitoring oxygen tension, wherein the skin tissue is heated to 43° C. for 10 minutes, where after the temperature is maintained at 43° C. for another 5 minutes while monitoring the oxygen level, followed by 30 minutes where the temperature is lowered to 41° C., where after the programs starts over. The nurse is well aware, that the most reliable measures of the oxygen tension is received only during the 5 minutes of measuring at 43° C., but is also notified of this on the monitoring screen. However to reduce the risk of injuries due to the higher temperature, she accepts this compromise.

After 12 hours, the NICU doctor and nurse looks at the data collected over the last 12 hours. From the data it appears that the situation, although still critical, is stable. Hence they decide to increase the time where the skin is heated to the lower temperature of 41° C. to 60 minutes, to further reduce the risk of injuring the skin. The nurse now programs the monitor accordingly. The trend within the field of cutaneous/transcutaneous blood gas sensors is generally to decrease the size of both sensors and monitors. A preferred site for measuring the transcutaneous partial pressure of blood gases is the earlobe, since the skin at the earlobe is very thin. Since the earlobe often has a small surface area, the sensor size is important. Furthermore, measuring the transcutaneous partial pressure of oxygen and carbon dioxide is often used on preterm neonates. Here the size of the sensor is even more important.

The invention claims a first and a second time interval of a time cycle. Despite the wording of a first and a second time interval, the skilled person will understand that the invention covers both scenarios where the cycle is started with the first time interval, and where the cycle is started with the second time interval.

The proposed system and method may be used for any sensor type for measuring blood gases e.g. electro chemical, optical or other types.

The invention claimed is:

1. A method for monitoring a transcutaneous partial pressure of oxygen ($tcpO_2$) at a measuring site of a patient, comprising:
    providing a sensor for measuring the $tcpO_2$, wherein the sensor comprises a heating element for heating skin of the patient;
    securing the sensor to the skin of the patient, such that the sensor defines the measuring site on the patient; and
    performing a $tcpO_2$ measuring cycle repetitively at the measuring site, wherein the $tcpO_2$ measuring cycle comprises:
        heating the site to a first temperature in a range of 35° C. to 42° C. during a first time interval,
        after the first time interval, heating the measuring site to a second temperature to thereby permeabilize the skin to oxygen in an outward direction from tissue or blood of the patient to the sensor,
        maintaining the second temperature without erythema to the skin of the patient during a second time interval that is shorter than the first time interval,
        after the second time interval, measuring the $tcpO_2$ at the site during a third time interval until consistent $tcpO_2$ measurements are obtained,
        determining a $tcpO_2$ level in the patient using the consistent $tcpO_2$ measurements,
        reporting the $tcpO_2$ level in the patient, and allowing the skin at the measuring site to cool before repeating the tcpO$_2$ measuring cycle.

2. The method according to claim 1, further comprising measuring a partial pressure of CO$_2$ continuously.

3. The method according to claim 2, wherein the measuring of the partial pressure of CO$_2$ takes the first and second temperatures into account.

4. The method according to claim 1, wherein the tcpO$_2$ measured during the third time interval is displayed at a monitor during a following first time interval of a subsequent tcpO$_2$ measuring cycle.

5. The method according to claim 1, wherein the second temperature is at least 41° C.

6. The method according to claim 1, wherein the second temperature is at least 43° C.

7. The method according to claim 1, wherein the second time interval is at least 10 minutes.

8. The method according to claim 1, wherein the third time interval is 5 minutes.

* * * * *